United States Patent [19]

Skrabanja et al.

[11] Patent Number: 6,040,301
[45] Date of Patent: *Mar. 21, 2000

[54] ORAL LIQUID ANTIDEPRESSANT SOLUTION

[75] Inventors: Arnold Titus Philip Skrabanja, Wageningen, Netherlands; Robert Edward Tully, Ilkley, United Kingdom

[73] Assignee: Akzo Nobel, N.V., Arnhem, Netherlands

[*] Notice: This patent issued on a continued prosecution application filed under 37 CFR 1.53(d), and is subject to the twenty year patent term provisions of 35 U.S.C. 154(a)(2).

[21] Appl. No.: 09/283,945

[22] Filed: Apr. 1, 1999

[30] Foreign Application Priority Data

Apr. 2, 1998 [EP] European Pat. Off. ............... 98201037

[51] Int. Cl.$^7$ .............................. A01N 43/46; A61K 31/55
[52] U.S. Cl. .......................... 514/214; 514/213; 514/215; 514/922; 514/970; 514/973; 514/994
[58] Field of Search ..................................... 514/213, 214, 514/215, 922, 970, 973, 974

[56] References Cited

U.S. PATENT DOCUMENTS 4,062,848  12/1977  van der Burg ................... 260/268 PC
5,208,261  5/1993   Van Den Oetelaar et al. ......... 514/646
5,238,688  8/1993   Beuving et al. ........................ 424/499

FOREIGN PATENT DOCUMENTS 0 436 252  10/1991  European Pat. Off. .
0 431 663  12/1991  European Pat. Off. .

OTHER PUBLICATIONS

Davis R et al., *Mirtazapine A Review of its Pharmacology and Therapeutic Potential in the Management of Major Depression,* vol. 5, No. 2, May 1, 1996,. pp. 389–402.

Mattila M et al., Actions and Interactions of Psychotropic Drugs on Human Performance and Mood: Single Doses or Org 3770, Amitriptyline, and Diazepam, Pharmacology and Toxicology, vol. 65, No. 2, Aug. 1, 1989, pp. 81–88.

Primary Examiner—Frederick Krass
Attorney, Agent, or Firm—Mary E. Gormley

[57] ABSTRACT

For the oral administration of the anti-depressant mirtazapine an aqueous solution or suspension is found which is preferably stabilized by methionine, is thickened, and which has a pH of from 2.5 to 3. By the formulation according to the invention, an undesirable local anesthetic effect of mirtazapine is avoided.

11 Claims, No Drawings

ORAL LIQUID ANTIDEPRESSANT SOLUTION

FIELD OF THE INVENTION

The invention is in the field of pharmaceutical compositions for peroral administration, comprising mirtazapine as a medicinally active ingredient. Mirtazapine (Remeron®) is known as a medicine for the treatment of, inter alia, depression.

BACKGROUND OF THE INVENTION

Pharmaceutical preparations which provide a peroral dosage form of mirtazapine are known in the form of tablets having strengths of the medicinally active ingredient of from 15 to 45 mg mirtazapine.

Although the known tablets are generally acceptable as far as their medicinal activity is concerned, the solid dosage form imposes restrictions on the pharmaceutical use of mirtazapine. Some patient populations have a difficulty, physical or psychological, in swallowing solid dosage forms. If a liquid dosage form were available, these patients could more easily take the required dose of mirtazapine, having it administered in the form of an oral liquid preparation.

In general, stabilised solutions of several antidepressants, including mirtazapine, in admixture with water and methionine, and not restricted to any particular concentration of mirtazapine, are known from EP 431 663. Although these solutions are stable and are suitable, in principle, for both parenteral and oral administration, a further improvement in the specific case of peroral administration of mirtazapine is desired. For, in the case of mirtazapine, a specific problem resides in that a local anaesthetic effect is experienced upon peroral administration of a solution within the general disclosure of EP 431 663, specifically having a concentration of mirtazapine of higher than 5 mg/ml. It is an object of the present invention to overcome this problem.

SUMMARY OF THE INVENTION

To this end, the invention is a solution or suspension of mirtazapine in admixture with water and preferably a stabiliser, characterised by having a concentration of mirtazapine in the range of from 5 to 110 mg/ml, a pH in the range of from 2.0 to 3.5, and comprising a thickening agent. Preferably, the solution also comprises a taste-masking agent.

Surprisingly, it was found that the bio-availability of mirtazapine in the oral solution or suspension according to the invention is equal to that of the known tablets. The daily doses of mirtazapine to be prescribed in both cases thus being equal, is of great benefit to medical practitioners. This is an unpredictable and unexpected property of the specific compound mirtazapine, that could not be foreseen from the disclosure in EP 431 663, in which the specifically exemplified mirtazapine solution has a concentration typical for parenteral administration. This renders mirtazapine a surprisingly suitable compound for use in the manufacture of an oral solution for the treatment of depression, in which treatment mirtazapine is administered in a dose of at least 15 mg per day. To this end, the concentration of mirtazapine in the oral solution to be manufactured preferably is n times 15 mg/ml, with n being an integer of from 1 to 3. Most preferably, the concentration is 15 mg/ml.

The oral solution according to the invention can be prepared by simply dissolving mirtazapine and preferably the stabiliser, in water, adding a thickening agent, adjusting the pH by the addition of a suitable amount of a pharmaceutically acceptable acid or, if necessary, re-adjustment by adding a suitable amount of a pharmaceutically acceptable base, and adding, optionally, any further ingredients such as taste-masking and flavour-improving agents.

DETAILED DESCRIPTION OF THE INVENTION

Mirtazapine, 1,2,3,4,10,14 β-hexahydro-2-methylpyrazo[2,1-a]pyrido[2,3-c][2] benzazepine, as referred to in this description is intended to include the compound per se as well as pharmaceutically acceptable salts thereof. The compound may be prepared as disclosed in U.S. Pat. No. 4,062,848 to van der Burg. It will be appreciated that mirtazapine contains a centre of chirality. The present invention includes each of the individual (R) and (S) enantiomers of mirtazapine and it salts in a form substantially free from the other enantiomer (i.e. having an enantiomeric purity of greater than 95% and preferably greater than 99%), as well as mixtures of the enantiomers in any proportion including a racemic mixture. As indicated above, the concentration of mirtazapine may be within a range of from 5 mg/ml to 110 mg/ml for the sake of optimum stabilisation by methionine as per EP 431 663. It is preferred, in view of the aforementioned surprising bioavailability of mirtazapine in oral solution, if the concentration mirtazapine is 10–50 mg/ml and most preferably 15 mg/ml.

The pH of the solution should be adjusted to a value in the range of from 2.0 to 3.5, preferably of from 2.5 to 3 and most preferably about 3. Such a low pH is essential for obtaining a stable solution satisfying the object of the invention. Too low a pH is undesirable due to irritation of the oesophagus (e.g. heartburn). Too high a pH will fail to avoid the undesired local anaesthetic effect. The available pharmaceutically acceptable acids and, if necessary, bases, are known to the person skilled in the art, e.g. glycine/HCl, potassium biphthalate/HCl, and citric acid, the latter being the preferred pH-adjusting agent.

Any of the thickeners common in the art can be used to increase the viscosity of the oral solution according to the invention. Bulk-sweetening agents may also serve this purpose, e.g. sugar and other non-sucrose bulk sweeteners (e.g. sorbitol, mannitol, hydrogenated glucose syrup, xylitol, maltitol). Polymers such as sodium carboxy methyl cellulose, xanthan gum, hydroxy propyl methyl cellulose, etc. are also suitable. The main limitation to the choice of thickeners is their stability at the low pH of the solution according to the invention. Preferred thickeners are bulk sweetening agents, a maltitol solution being most preferred as it has a slightly greater viscosity than others such as sorbitol, and also gives a better mouthfeel. It may be possible to give an acceptable mouthfeel by using an artificial sweetener, e.g. aspartame or saccharin. Sucrose is generally avoided, as it causes dental caries.

Stabilisers, other than the preferred methionine, e.g. antioxidants such as cysteine, ascorbic acid and β-mercaptoethanol, can be employed. However, as per the disclosure in EP 431 663, methionine is strongly preferred. In line with this teaching, the stabiliser should be present in an amount sufficient to stabilise the mirtazapine in aqueous solution for a desired time at a desired temperature, e.g. 2 years at 25° C. Preferably, the amount of methionine is within the range of from 15 to 20% by weight calculated on the amount of mirtazapine. Most preferably, 0.5 mg/ml methionine is employed per 3 mg/ml of mirtazapine.

The carrier liquid for the oral solution of the invention is water. This water component may comprise any suitable, conventional additive, such as flavours, sweeteners, and colouring agents. Among the flavours, citrus is preferred, as these flavours are ideally compatible with the base flavour of the product. The most preferred flavour is orange tangerine, as this surprisingly well suppresses the bitter taste that mirtazapine has. As a further additive, a preservative may be present. E.g. paraben esters or, preferably, benzoic acid or a benzoate salt such as Na-benzoate.

The oral solution or suspension according to the invention can also be produced starting from a pharmaceutical formulation comprising mirtazapine, which formulation comprises means to produce the solution or suspension according to the invention within 60 seconds after having been brought into contact with an amount of water in the range of from 0.5 to 400 mL. Such means can be the admixture into the formulation of agents which rapidly expand and dissolve upon contact with water or which produce gases upon contact with water. The result is that the formulation rapidly disintegrates to a suspension which can further enable fast dissolution of the mirtazapine. The water which is added to the formulation leading to its disintegration can be from any fluid suitable for consumption and containing water. Furthermore, the saliva of the person to be treated may also be the water containing fluid leading to rapid disintegration of the formulation in the mouth of the person, who can then swallow the formulation as a solution or suspension. The formulation is composed such as to ensure that the solution or suspension arising in the mouth has the characteristics of a solution or suspension according to this invention. The required amount of water can easily be estimated on basis of the absolute quantity of mirtazapine in the pharmaceutical formulation. Of course, when the formulation is intended for a solution or suspension arising in the mouth the amount of saliva available until the solution or suspension can be swallowed is estimated to be small, but at least 0.5 mL, whereas the amount of water should be more voluminous, whereby 400 mL is considered to be a an upper limit, when the formulation is intended to be for oral intake of a single dosage. For the latter purpose the preferred range is 1 to 200 mL, and most preferred 2 to 100 mL. The means to produce the solution or suspension according to the invention within 60 seconds after contact of the pharmaceutical formulation with water are well-known to the person skilled in the art. The formulation can be made to disintegrate rapidly with water by addition of swelling and water-disintegratable compounds, such as for example carboxymethylcellulose, compressible carbohydrates like mannitol, sorbitol, dextrose, sucrose, xylitol, lactose or mixtures thereof, or by addition of effervescent agents such as the combination of carbonate salts and crystalline acids, like sodium bicarbonate and citric acid, respectively.

The oral solution of mirtazapine according to the invention can be administered in any manner suitable for the administration of oral solutions, i.e. by swallowing the required amount from a spoon, from a bottle, via a straw, or else. In view of the desire to provide an exact dose, it is preferred that the solution is administered from a container provided with means to dispense accurately the proper dose, e.g. 1–3 ml in the case of a mirtazapine concentration of 15 mg/ml. Preferably, said means is in the form of a dispensing pump of a type not uncommon to liquid soap-containers.

For a further disclosure of aqueous solutions, suspensions and rapidly water disintegrating formulations reference is made to *Remington's Pharmaceutical Sciences,* 18th edition (1990), pages 1521 to 1530.

The invention will be further explained with reference to the following Examples.

EXAMPLE 1

A solution according to the invention was prepared by admixing the following ingredients:

| | |
|---|---|
| mirtazapine | 15.0 mg |
| L-methionine | 2.6 mg |
| sodium benzoate | 1.2 mg |
| saccharin sodium | 1.2 mg |
| citric acid monohydrate | 40.0 mg |
| glycerol | 75.0 mg |
| maltitol solution | 700 mg |
| purified water | to 1.0 mL |

The solution has a pH of 3 and is thickened.

EXAMPLE 2

An oral solution according to the invention was prepared as in Example 1. The formulation was identical, except for the addition of 5.0 mg of Orange Tangerine 10889-56 flavour.

TEST EXAMPLE

The solutions of Examples 1 and 2 were used in a randomised study with a balanced parallel group design. Overall, 30 healthy volunteers were treated. Each of three treatments were administered to ten subjects (5 males, 5 females). Said treatments were:

A) 1 mL of the formulation according to Example 1 (15 mg of mirtazapine).

B) 1 mL of the formulation according to Example 2 (15 mg of mirtazapine).

C) 1 mL of B diluted to 50 mL of water (15 mg of mirtazapine).

After administration, the subjects had to fill in a taste questionnaire.

Results

Treatment A was experienced as unacceptable by four subjects, as neither unacceptable, nor acceptable by four subjects, as very unacceptable by one subject, and as acceptable by one subject. Most subjects disliked the taste of the solution and would not prefer to take this medication every day. None of the subjects experienced a local anaesthetic effect upon administration of treatment A.

Treatment B was experienced as acceptable by five subjects, as neither unacceptable, nor acceptable by two subjects, as unacceptable by two subjects, and as very acceptable by one subject. Most subjects did not really like the taste of the solution, but would not mind taking this medication every day. None of the subjects experienced a local anaesthetic effect upon administration of treatment B.

Treatment C was experienced as acceptable by five subjects, as neither unacceptable, nor acceptable by one subjects, as very acceptable by two subjects. One subject dropped out, one subject was very positive about the solution, but marked the box "very unacceptable." This score was not included. Some subjects did not dislike the taste of the solution some subjects did not like the taste, but would not mind taking this medication every day. None of the subjects experienced a local anaesthetic effect upon administration of treatment C.

COMPARATIVE EXAMPLE

A solution was prepared basically following Example 1 of EP 431 63, with the concentration of mirtazapine being 6.0 mg/mL. The pH of the solution is 4. The solution is unthickened. The solution was administered to a group of 6 healthy volunteers. None of the subjects liked the taste of the solution. All of the subjects experienced a local anaesthetic effect.

We claim:

1. A solution or suspension of mirtazapine in admixture with water having a concentration of mirtazapine in the range of from 5 to 110 mg/mL, a pH in the range of from 2.0 to 3.5, and comprising a thickening agent.

2. A solution or suspension according to claim 1, wherein the solution comprises a stabiliser.

3. A solution or suspension according to claim 2, wherein the stabiliser is selected from the group consisting of L-methionine, D-methionine, LD-methionine, and mixtures thereof.

4. A solution or suspension according to claim 1, wherein the concentration of mirtazapine is of from 10–50 mg/mL.

5. A solution or suspension according to claim 3, wherein the amount of methionine is within the range of from 15 to 20% by weight calculated on the amount of mirtazapine.

6. A solution or suspension according to claim 1, wherein the pH is of from 2.5 to 3.

7. A solution or suspension according to claim 1, wherein the thickening agent is maltitol.

8. A solution or suspension according to claim 1, further comprising a taste-masking agent.

9. A solution or suspension according to claim 8, wherein the taste-masking agent has an orange tangerine flavour.

10. A method for treating depression, comprising administering to a patient a solution or suspension according to claim 4.

11. The method of claim 10, wherein a dosage of at least 15 mg mirtazapine per day is administered.

* * * * *